United States Patent [19]

Takatsuto et al.

[11] Patent Number: 5,763,366
[45] Date of Patent: Jun. 9, 1998

[54] BRASSINOSTEROID DERIVATIVE AND PLANT GROWTH REGULATOR USING THE SAME

[75] Inventors: Suguru Takatsuto, Niigata; Yasuo Kamuro, Aichi; Tsuyoshi Watanabe; Hiroki Kuriyama, both of Kanagawa, all of Japan

[73] Assignee: TAMA Biochemical Co. Ltd., Tokyo, Japan

[21] Appl. No.: 556,923

[22] PCT Filed: May 31, 1994

[86] PCT No.: PCT/JP94/00881

§ 371 Date: Nov. 29, 1995

§ 102(e) Date: Nov. 29, 1995

[87] PCT Pub. No.: WO94/28011

PCT Pub. Date: Dec. 8, 1994

[30] Foreign Application Priority Data

Jun. 1, 1993 [JP] Japan .................................. 5-130826

[51] Int. Cl.⁶ .......................... A01N 43/22; C07D 407/08
[52] U.S. Cl. .......................... 504/291; 549/268
[58] Field of Search .......................... 549/268; 504/291

[56] References Cited

U.S. PATENT DOCUMENTS 4,961,775  10/1990  Takatsuto et al. .................. 71/88

FOREIGN PATENT DOCUMENTS 1-313401  12/1989  Japan .
2 127 022  4/1984  United Kingdom .............. C07J 73/00

*Primary Examiner*—Bernard Dentz
*Attorney, Agent, or Firm*—Limbach & Limbach L.L.P.

[57] ABSTRACT

Brassinosteroid derivatives expressed in formula (I) and formula (II)

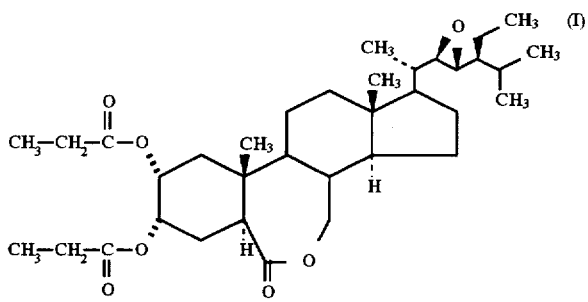

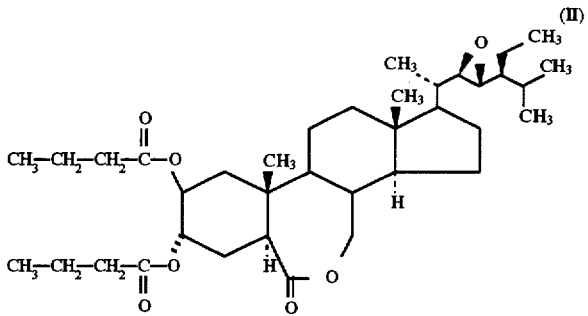

and a plant growth regulator containing one type or two types of these brassinosteroid derivatives as active ingredient.

The invention thereby presents novel brassinosteroid analogous compounds expressed in formula (I) and formula (II) and a plant growth regulator containing these compounds showing a persisting plant growth regulating action.

9 Claims, No Drawings

BRASSINOSTEROID DERIVATIVE AND PLANT GROWTH REGULATOR USING THE SAME

This application is a 371 PCT/JP94/00881 filed May 31, 1994.

TECHNICAL FIELD

The present invention relates to novel brassinosteroid derivatives, and a plant growth regulator using them as active ingredients.

BACKGROUND ART

Brassinolide was discovered from rape pollen as plant growth regulating substance by M. D. Grove et al. in 1979 [Nature, Vol. 281, pp. 216–217 (1979)], and ever since the plant growth promoting effects of brassinolide and brassinosteroid analogous compounds have been disclosed ("Brassinosteroids. Chemistry, Bioactivity & Applications." ACS Symposium Series 474, American Chemical Society, Washington, D.C., 1991). In this relation, Japanese Laid-open Patent No.1-125396 was disclosed.

However, brassinolide so far known to have the highest physiological activity and brassinosteroid analogous compounds do not produce stable effects in practical use and have not been actually utilized at the present.

It is hence an object of the invention to present a novel brassinosteroid derivative excellent in practical use in the effect and duration of plant growth promoting action by solving the above problem.

DISCLOSURE OF THE INVENTION

The invention presents a brassinosteroid derivative expressed in formula (I).

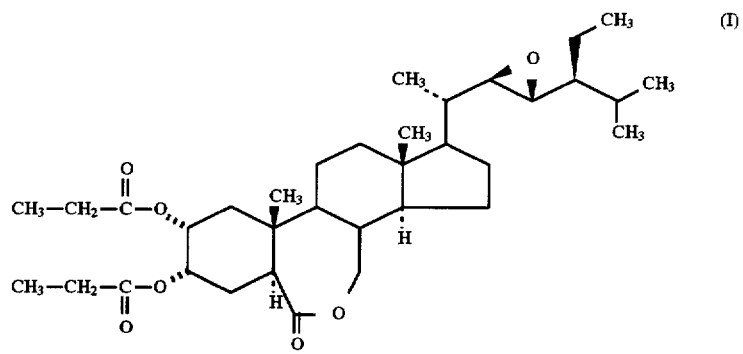

The invention also presents a brassinosteroid derivative expressed in formula (II).

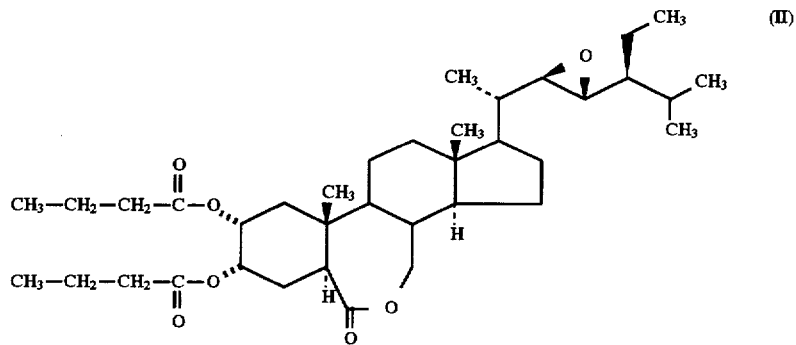

Moreover, the invention presents a plant growth regulator containing one type or two types of brassinosteroid derivatives expressed in formula (I)

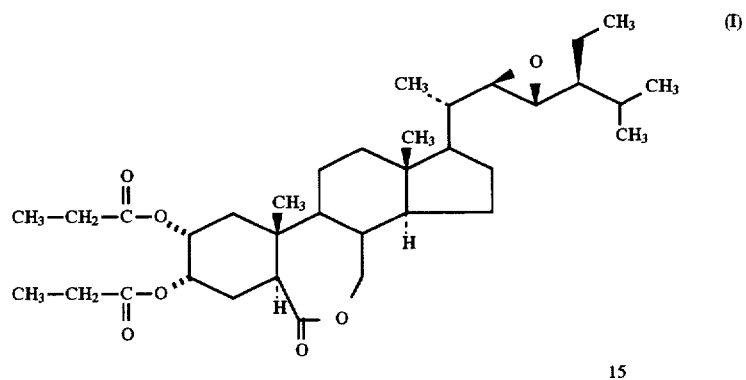

and formula (II)

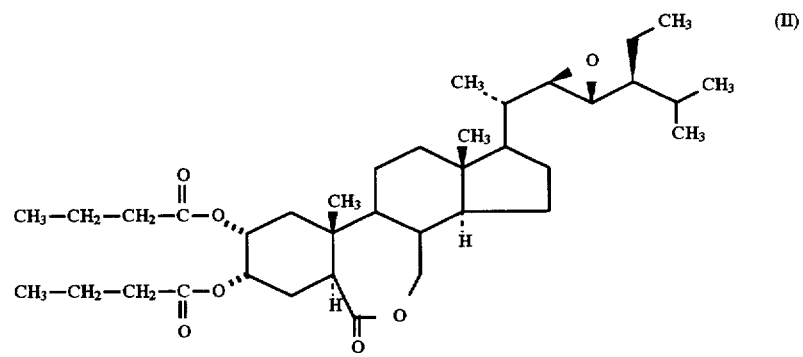

as active ingredient.

Novel brassinosteroid analogous compounds having a plant growth regulating activity expressed as compound (I) and compound (II) and the plant growth regulator containing them as active ingredients, presented by the invention, are useful because they show plant growth regulating actions on various plants with an excellent durability.

BEST MODE OF CARRYING OUT THE INVENTION

The invention is specifically described below.

The compound of formula (I) of the invention [hereinafter called compound (I)] and compound of formula (II) [hereinafter called compound (II)] are capable of enhancing the yield of dihydroxyl formation of 2α-position and 3α-position, by adjusting the amount of reaction agent, when performing catalytic hydroxyl formation of (22E, 24S)-24-ethyl-5α-cholesta-2,22-diene-6-one [hereinafter called compound (III)] [K. Mori, Agric. Biol. Chem., 44(5), 1211(1980)] by a catalytic amount of osmium tetroxide, in the presence of t-butylhydroperoxide or N-methylmorpholine-N-oxide, in inert gas such as nitrogen and argon. Thus obtained 2α position, 3α position dihydroxy forms (IV) are dissolved in pyridine containing 4-dimetnylaminopyridine to react with propionic anhydride or butyric anhydride, and then (V) is obtained in the case of propionic anhydride, or (VI) in the case of butyric anhydride. This (V) or (VI) is dissolved in chlorine derivative organic solvent which is stable in oxidation, and is oxidized in organic peroxide, for example, perbenzoic acid, m-monochloroperbenzoic acid, m-monobromoperbenzoic acid, monoperphthalic acid, trifluoroperacetic acid, and their sodium salt or potassium salt, so that compound (I) is obtained from (V), or compound (II) from (VI).

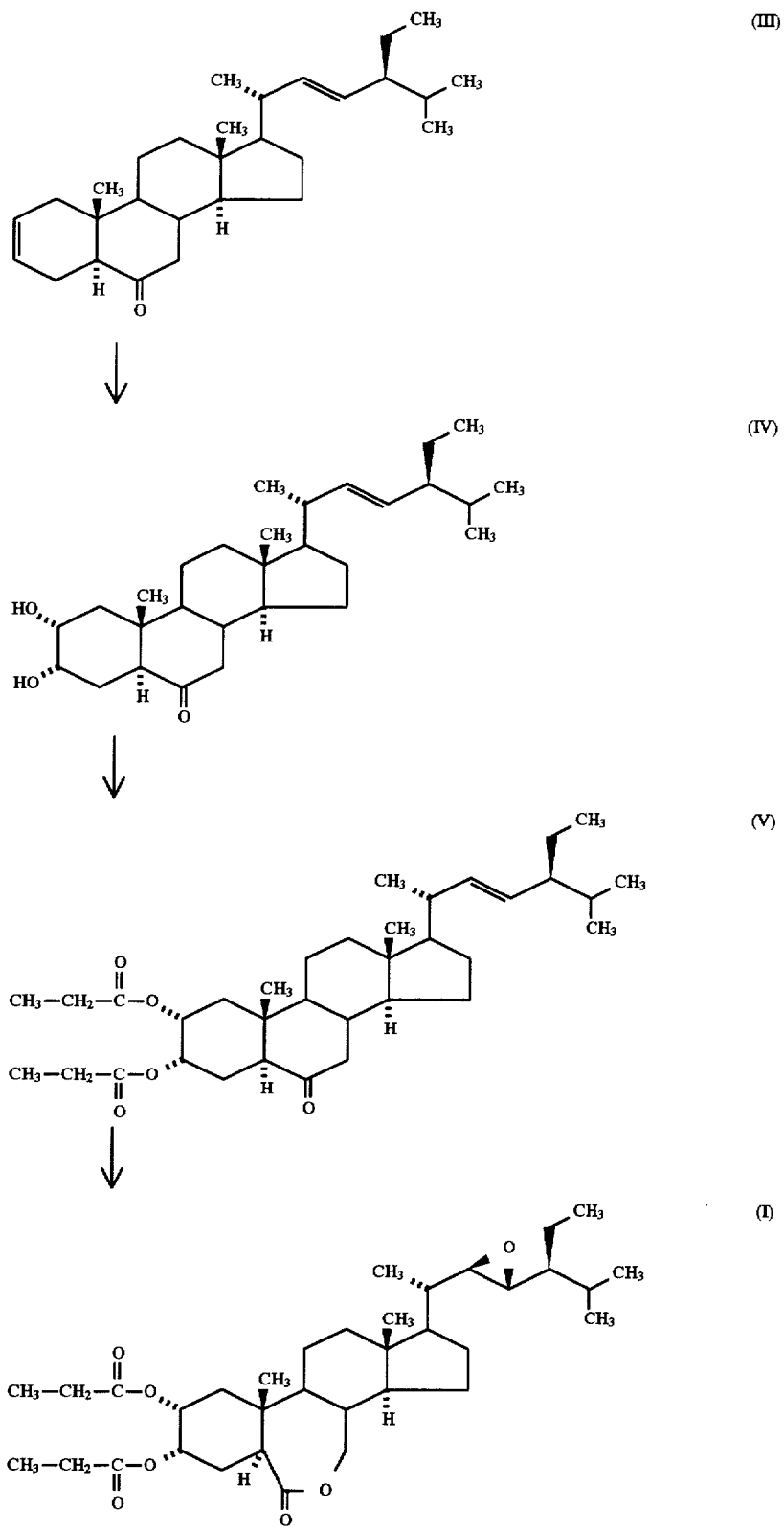

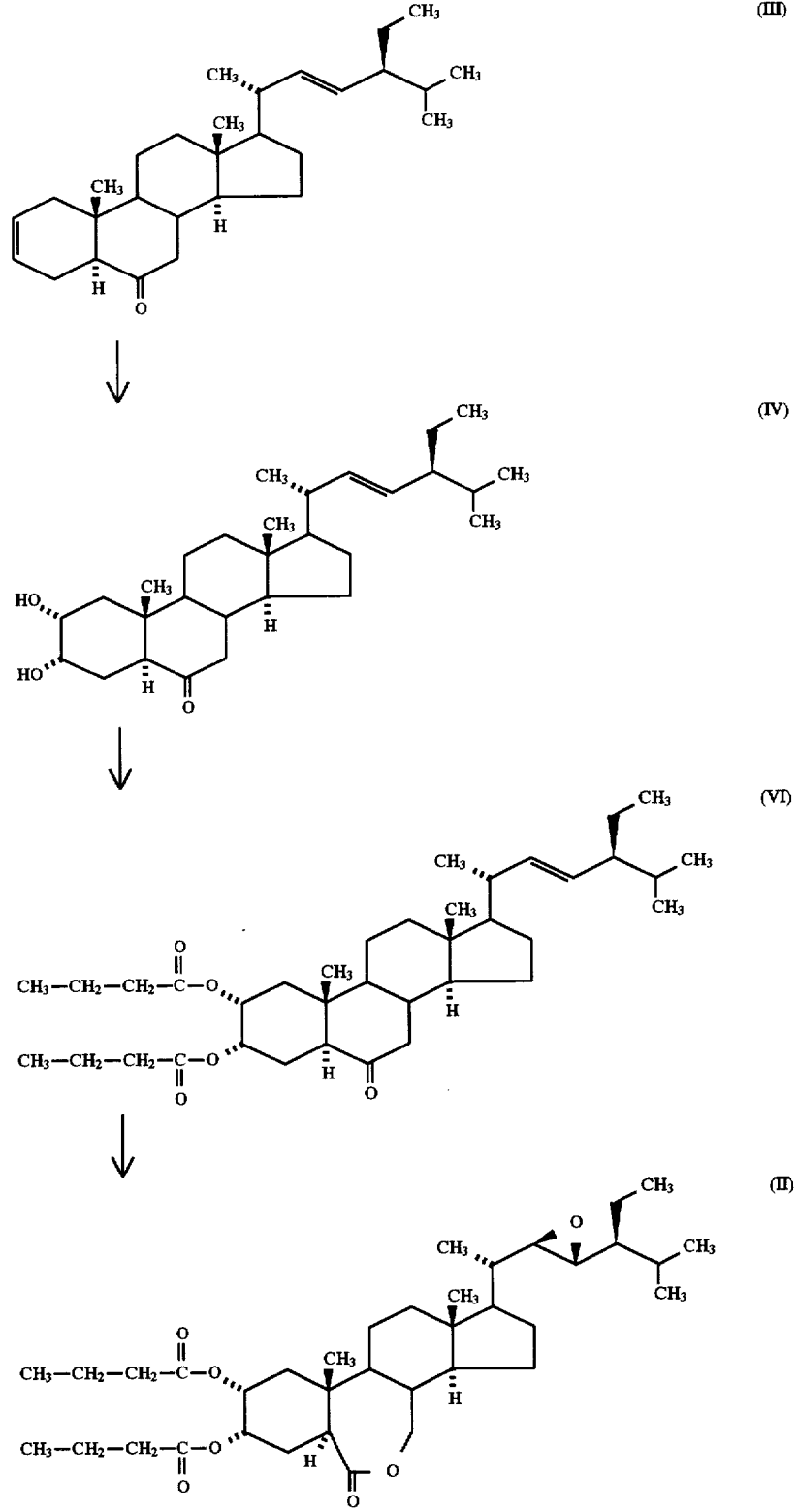

The compound (I) and compound (II) of the invention exhibit favorable actions on plants. For example, by treating with chemicals in the seed or growing period of plants, growth promoting effect, disease resisting effect, chemical injury lessening effect by herbicide, bactericide or insecticide, chemical injury lessening effect by salts, injury lessening effect by low temperature or high temperature stress, moisture stress lessening effect, and the like may be achieved. By treating with chemicals around the blossoming season of plants, the crop will be increased and the quality will be improved in rice, wheat, corn and other gramineous crops, soybean, kidney bean, and other pulse crops, potato, sugarcane, and other tubers, rape and other brassicaceous crops. When melon, watermelon, cucumber, and other cucurbitaceous crops, or tomato, eggplant, and other solanaceous crops are treated with chemicals, the crop will be increased, and the taste, shape and other quality elements will be enhanced. It is also a feature of these compounds that they have no injury on plants.

When using these compounds as plant growth regulators of crops, they may be used either alone or in mixture.

When using the compounds of the invention as plant growth regulators, they may be mixed with other plant hormones or agricultural chemical aids, for example, spreading agent, emulsifier, wetting agent, dispersant, binding agent, and disintegrating agent, and may be used in the dosage form of powder, granules, tablets, solids, wettable powder, emulsion, or liquid.

The compounds of the invention adjusted in various forms are not uniform, depending on the crop plant, treating area, treating method, treating time or season, and can be determined properly, and although not limited, generally, an effective method is immersion method as pretreatment of seeding or planting, spraying method on stem leaves, flowers, fruits, and plant cultivating soil in the treatment of plants during growth period, or coating or injecting method.

The application concentration varies with the crop plant, treating method, treating time and period, and dosage form, but usually when prepared in aqueous solution, the concentration of the active ingredients should be $1 \times 10^{-5}$ ppm to 1 ppm, preferably $1 \times 10^{-3}$ ppm to $1 \times 10^{-1}$ ppm.

The compounds of the invention may be used either alone, or in mixture with insecticide, fungicide, herbicide, or fertilizer.

The invention is described below by referring to embodiments. It must be however noted that the technical field of the invention is not limited by these embodiments alone.
(Embodiment 1)

Synthesis of 2α, 3α-dipropionyloxy-24S-ethyl-5α-cholest-22-ene-6-one (V)

To 20.5 g (49.92 mmol) of (22E, 24S)-24S-ethyl-5α-cholesta-2, 22-diene-6-one (III) [K. Mori, Agric. Biol. Chem., 44, 1211 (1980)], 7.3 g (54.42 mmol) of N-methylmorpholine-N-oxide and 1000 ml of acetone were added and stirred. After purging the reaction container with nitrogen gas, a mixed solution of 22 ml of water and 32 ml of t-butyl alcohol containing 390 mg (1.5 mmol) of osmium tetroxide was added to react overnight at room temperature. Filtering the crystals (15.6 g) precipitating in the reaction solution, the filtrate was stirred for 1 hour by adding aqueous solution of sodium hydrogensulfite, and extracted by chloroform, washed in water, and dried on anhydrous magnesium sulfate, and the solvent was distilled away in vacuo, and crude product was obtained. This crude product was refined by silica gel column chromatography (toluene:ethyl acetate 30:1), and 3.77 g of 2α, 3α-dihydroxy-24S-ethyl-5α-cholest-22-ene-6-one (IV) was obtained. Combining with the previously filtered crystals (19.37 g), 150 ml of pyridine, 76 ml of propionate anhydride, and 500 mg of 4-dimethylaminopyridine were added to react overnight at room temperature. Extracting with chloroform, washing in water, and drying on anhydrous magnesium sulfate, the solvent was distilled away in vacuo, and crude product was obtained.

This crude product was defined by silica gel column chromatography (benzene, ethyl acetate 30:1 to 15:1), and 21.06 g (75.7%) of 2α, 3α-dipropionyloxy-24S-ethyl-5α-cholest-22-ene-6-one (V) was obtained.

Crystal: Acicular
mp: 128°–129° C. (acetone)
Rf value: 0.48 TLC plate (Merck-made, 1.5 cm×6.7 cm, Kieselgel 60F$_{254, 0.25}$ mm film thickness, Art. 5715), hexane-ethyl acetate, 4:1 v/v
$^1$H-NMR(CDCL$_3$) δ(ppm): 0.72 (3H, S), 1.10 (3H, t), 1.16 (3H, t), 2.58 (1H, m), 4.97 (1H, m), 5.09 (2H, m), 5.40 (1H, m).
(Embodiment 2)

Synthesis of (22R, 23R, 24S)-2α, 3α-dipropionyloxy-22, 23-epoxy-B-homo-7-oxa-5α-sti [compound (I)]

Dissolving 2.06 g (3.70 mmol) of 2α, 3α-dipropionyloxy-24S-ethyl-5α-cholest-22-ene-6(V) obtained in embodiment 1 in 100 ml of dichloromethane, 8.0 g (31.08 mmol) of m-chloroperbenzoic acid was added, and the mixture was stirred for 15 days at room temperature. Afterwards, adding 8.0 g of powder calcium hydroxide, stirring for 1 hour and filtering, the solvent was distilled away in vacuo, and crude product was obtained. This crude product was refined by silica gel column chromatography (benzene:ethyl acetate 30:1 to 15:1), and 0.85 g (39.0%) of (22R, 23R, 24S)-2α, 3α-dipropionyloxy-22, 23-epoxy-B-homo-7-oxa-5α-s [compound (I)] was obtained.

Crystal: Acicular
mp: 147°–148° C. (methanol)
Rf value: 0.23 TLC plate (Merck-made, 1.5 cm×6.7 cm, Kieselgel 60F$_{254, 0.25}$ mm film thickness, Art. 5715), benzene-ethyl acetate, 10:1 v/v
FD-MS: m/z 589 (M$^+$+1)
$^1$H-NMR(CDCl$_3$)δ(ppm): 0.72 (3H, S), 1.10 (3H, t), 1.18 (3H, t), 2.73 (1H, dd), 3.00 (1H, dd), 4.10 (2H, m), 4.89 (1H, m), 5.38 (1H, m).
(Embodiment 3)

Synthesis of (22R, 23R, 24S)-2α, 3α-dibutyroyloxy-22, 23-epoxy-B-homo-7-oxa-5α-stigm [compound (II)]

Same as in embodiment 1, to 8.3 g of 2α, 3α-dihydroxy-24S-ethyl-5α-cholest-22-ene-6(IV) obtained by treating 10.0 g (23.45 mmol) of (22E, 24S)-24S-ethyl-5α-cholesta-2, 22-diene-6-one (III) same as in embodiment 1, 100 ml of pyridine, 40 ml of butyric anhydride, and 300 mg of 4-dimethylaminopyridine were added to react overnight at room temperature. After extracting by chloroform, washing in water, and drying on anhydrous magnesium hydroxide, the solvent was distilled away in vacuo, and crude product was obtained. This crude product was refined by silica gel column chromatography (benzene:ethyl acetate 30:1 to 15:1), and 10.0 g (72.9%) of 2α, 3α-dibutyroyloxy-24S-ethyl-5α-cholest-22-ene-6 (VI) was obtained.

mp: 101°–102° C. (methanol)
$^1$H-NMR(CDCl$_3$)δ(ppm): 0.69 (3H, S), 0.93 (3H, t), 0.97 (3H, t), 2.56 (1H, m), 4.97 (1H, m), 5.09 (2H, m), 5.40 (1H, m).

Crystal: Acicular
Rf value: 0.51 TLC plate (Merck-made, 1.5 cm×6.7 cm, Kieselgel 60F$_{254, 0.25}$ mm film thickness, Art. 5715), hexane-ethyl acetate, 4:1 v/v Treating 2.0 g of 2α, 3α-dibutyroyloxy-24S-ethyl-5α-cholest-22-ene-6-one (VI) same as in embodiment 2, 640 mg (30.3%) of (22R, 23R, 24S)-2α, 3α-dibutyroyloxy-22, 23-epoxy-B-homo-7-oxa-5α-stigmastane-6-o [compound (II)] was obtained.

Crystal: Amorphous
Rf value: 0.49 TLC plate (Merck-made, 1.5 cm×6.7 cm, Kieselgel 60F$_{254, 0.25}$ mm film thickness, Art. 5715), benzene-ethyl acetate, 5:1 v/v FD-MS: m/z 617 (M$^+$+1)

$^1$H-NMR(CDCl$_3$) δ(ppm): 0.67 (3H, S), 0.99 (3H, S), 2.70 (1H, dd), 3.00 (1H, dd), 4.10 (2H, m), 4.86 (1H, m), 5.36 (1H, m).

(Embodiment 4)

Growth Promoting Effect of Radish

Compounds (I) and (II) were dissolved in ethanol individually, and solution of 100 ppm were prepared. Adding 2 ml of each ethanol solution to 20 L of water containing 4 ml of commercial spreading agent Guramin (Sankyo), and 1/100 ppm each of compounds (I) and (II) was adjusted, and chemical solutions were prepared. Compound A (Japanese Laid-open Patent No. 1-125396, No. 11) and brassinolide were similarly prepared to have a concentration of 1/100 ppm.

Radish was cultivated in an ordinary open field in June, and 10 L/are of chemical solution was applied uniformly in the initial root thickening period. On day 12 and day 24 after application, 30 stocks of excellent growth were sampled from each region, and the plant weight was measured by dividing into the leaf part and root part, and the mean individual weight was calculated. The percentage of the treated region to the control region is calculated and shown in Table 1.

TABLE 1

| Compound | 12 days after application | | 24 days after application | |
|---|---|---|---|---|
| | Root | Leaf | Root | Leaf |
| Brassinolide | 141.5 | 137.0 | 104.6 | 103.8 |
| Compound (I) | 104.9 | 103.7 | 118.2 | 110.7 |
| Compound (II) | 100.0 | 103.0 | 123.6 | 109.0 |
| Compound A | 102.5 | 103.6 | 110.9 | 105.0 |
| Control | 100 | 100 | 100 | 100 |

As a result, as shown in Table 1, in 12 days after application, brassinolide was most effective. In 24 days after application, however, the compounds (I) and (II) of the invention proved excellent, being followed by compound A (Japanese Laid-open Patent No. 1-125396, No. 11), and brassinolide, and hence the compounds (I), (II) of the invention are found to be excellent in duration of effect.

(Embodiment 5)

Germination and Growth Promoting Effect by Immersion Treatment of Rice Seeds.

From compounds (I) and (II), 1/100 ppm solutions were prepared as chemical solutions in the same manner as in embodiment 3. Compound B (Japanese Laid-open Patent No. 1-125396, No. 6) and brassinolide were similarly prepared at 1/100 ppm.

One hundred grains each of rice seeds (variety: Nipponbare) were immersed in 20 ml of each chemical solution (in 20 ml of water in control region) for 20 hours, and seeded in upland field in June (soil covering 1 cm).

When more than half of the seedlings were grown to the 4th leaf stage, the degree of growth was investigated, and the result is shown in Table 2.

TABLE 2

| Compound | Total number grown to the 4th leaf stage or more | Total number grown to the 3rd leaf stage or more |
|---|---|---|
| Brassinolide | 72 | 78 |
| Compound (I) | 85 | 90 |

TABLE 2-continued

| Compound | Total number grown to the 4th leaf stage or more | Total number grown to the 3rd leaf stage or more |
|---|---|---|
| Compound (II) | 83 | 88 |
| Compound B | 76 | 82 |
| Control | 58 | 66 |

As a result, the compounds (I) and (II) of the invention demonstrated an excellent germination and growth promoting effect in rice, better than the effect of compound B (Japanese Laid-open Patent No. 1-125396, No. 6).

(Embodiment 6)

Seed-Setting Promoting Effect in Rice

In each region of 1 are of paddy field, the following test was conducted by using paddy rice (variety: Nipponbare). The compounds (I), (II), A, and brassinolide were prepared in 1/1000 ppm solutions, and sprayed by 15 L/are each, using small spraying tool, in booting stage (August 3, one week before heading) and the end of flowering stage (August 22). When harvesting, 70 to 80 stocks were cropped from the treated regions and control region, and the mean head weight of each stock was investigated, and the ratio to control region was calculated. The result is shown in Table 3.

TABLE 3

| Compound | Ratio to control region of head weight per stock (%) |
|---|---|
| Brassinolide | 103.2 |
| Compound (I) | 111.0 |
| Compound (II) | 110.3 |
| Compound A | 105.7 |
| Control | 100.0 |

As known from Table 3, the head weight per stock, that is, the yield increased, and compound (I) indicated the highest effect, and compound (II) ranked the second, both superior to the effects of compound A and brassinolide.

(Embodiment 7)

Seed-Setting Promoting Effect in Corn

By conventional field cultivation of corn (variety: Honey Bandam), 1/100 ppm solutions of compounds (I), (II), A, and brassinolide were applied by 20 L/are in 5 days before start of staminate emergence and in full blossoming season. By conventional harvesting of female heads, 50 heads were selected at random from each region, and the length of the seed-setted portion was measured, and the mean length was calculated, of which result is shown in Table 4.

TABLE 4

| Compound | Means length of seed-setted portion of female head (cm) |
|---|---|
| Brassinolide | 17.3 |
| Compound (I) | 19.1 |
| Compound (II) | 19.8 |
| Compound A | 18.6 |
| Control | 17.1 |

The seed-setted portions in the regions treated by compounds (I) and (II) were longer than those in the regions treated by compound A and brassinolide, and the seed-setting promoting effect was noted.

(Embodiment 8)

Fruit-setting and thickening promoting effect in grape

Using mature trees by field cultivation of grape (variety: Delaware), 1/100 ppm each of compounds (I), (II), A and brassinolide was sprayed in each cluster in 7 days before start of blossoming. Harvesting in mature period, the mean cluster weight of each region was calculated, of which result is shown in Table 5.

TABLE 5

| Compound | Mean weight of harvested cluster (g) |
|---|---|
| Brassinolide | 150.1 |
| Compound (I) | 167.6 |
| Compound (II) | 176.3 |
| Compound A | 156.0 |
| Control | 148.9 |

The mean cluster weight in the regions treated by compounds (I) and (II) was larger than in the regions treated by compound A and brassinolide, and an excellent fruit-setting and thickening promoting effect was noted.

(Embodiment 9)

Growth and Yield Promoting Effect by Wheat Seed Treatment

Compounds (I), (II), A and brassinolide were dissolved in a solution of ethanol and water of 50 (vol.) by 50 (vol.) to a concentration of 0.01 ppm. In each solution, wheat seeds (variety: Norin No. 61) were immersed for 2 seconds, and dried in air. In the control region, seeds were similarly treated with ethanol and water, 50 (vol.) by 50 (vol.).

The treated seeds were conventionally seeded and cultivated in the field in November. In 2 months after seeding, 50 stocks were sampled at random from each region, and the mean plant weight and number of tillers/stock were investigated, and the mean head weight/stock was investigated when harvesting, and the results as shown in Table 6 were obtained.

TABLE 6

| Compound | Ratio to control region in 2 months after seeding (%) | | Ratio to control region of head weight/stock in harvesting period (%) |
|---|---|---|---|
| | Plant weight/stock | Number of tillers/stock | |
| Brassinolide | 103.3 | 102.7 | 103.0 |
| Compound (I) | 115.5 | 120.6 | 112.7 |
| Compound (II) | 118.9 | 124.1 | 115.6 |
| Compound A | 112.4 | 116.3 | 110.0 |
| Control | 100.0 | 100.0 | 100.0 |

As known from Table 6, the compounds (I) and (II) presented higher effects in both growth and yield, as compared with compound A and brassinolide.

(Embodiment 10)

Plant Cold Injury Preventive Effect

Compounds (I), (II), A and brassinolide were prepared in 0.01 ppm aqueous solution, and applied on benjamin tree having 150 to 200 leaves in pots cultivated in a greenhouse, and the pots were placed outdoors from the next day in late November.

After 30-day test, the number of leaves falling due to cold weather was counted, and the defoliation rate to the number of leaves counted at the start of the test was calculated, and the result is shown in Table 7.

TABLE 7

| Compound | Defoliation rate (%) |
|---|---|
| Brassinolide | 80.4 |
| Compound (I) | 39.7 |
| Compound (II) | 33.0 |
| Compound A | 45.3 |
| Control | 93.7 |

As clear from Table 7, the defoliation rate of compounds (I) and (I) was lower as compared with compound A and brassinolide, and a high cold injury preventive effect was proved.

(Embodiment 11)

Lessening Effect of Herbicide Chemical Injury (Growth Inhibition)

Three days before transplantation of paddy rice seedling (variety: Nipponbare), 0.01 ppm aqueous solution of compounds (I), (II), and brassinolide was sprayed by 100 liters per 10 ares.

To the treated seedlings, untreated seedlings were transplanted by five each in a pot of 1/5000 are, and grown in a greenhouse. In 5 days after transplantation, commercial herbicides Simetryn and Butachlor were applied in a pot by an equivalent of 5 kg ingredient/10 ares. In 20 days after treatment with herbicides, the transplanted seedlings were pulled out and dried, and the ratio to the region not treated with herbicide (%) was calculated and the growth degree in each region was compared, of which result is shown in Table 8.

TABLE 8

| Compound | Herbicide | | |
|---|---|---|---|
| | Simetryn | Butachlor | No herbicide |
| Brassinolide | 72.9 | 63.7 | 103.7 |
| Compound (I) | 90.1 | 85.5 | 110.2 |
| Compound (II) | 82.4 | 80.2 | 108.5 |
| Control | 60.3 | 43.8 | 100.0 |

As shown in Table 8, all compounds lessened the chemical injury (growth inhibition) by herbicides, and in particular the compounds (I) and (II) presented a superior chemical injury lessening effect to brassinolide.

(Embodiment 12)

Fruit-Setting Gromoting Effect by Lessening of Self-Incompatibility

Plums (variety: Sordam) were used in the test. In an ordinary conventional cultivation field, in 5 days before artificial pollination, 0.01 ppm aqueous solution of compounds (I), (II), and brassinolide was sprayed by an equivalent of 300 liters/10 ares.

Artificial pollination was tested by using pollen taken from a conventional pollinizer, and by self-pollination.

In 2 months after pollination, on the investigation branches in each test region, the number of fruits per pollen of pollination was surveyed, and the fruit-setting rate was calculated, of which result is shown in Table 9.

TABLE 9

| Compound | Fruit-setting rate by pollen from pollinizer (%) | Fruit-setting rate by self-pollination (%) |
|---|---|---|
| Brassinolide | 15.9 | 3.5 |
| Compound (I) | 30.6 | 13.1 |
| Compound (II) | 25.2 | 11.3 |
| Control | 14.7* | 0.4 |

*Conventional method

As compared with the number of fruits by the conventional method, the fruit-setting rate in compound treated regions was enhanced, and the compounds (I) and (II) were more effective than brassinolide. By application of the compounds (I), (II), the fruit-setting by self-pollination was equally comparable with the fruit-setting rate by pollen from pollinizer, and the compounds (I) and (II) of the invention exhibited effects of lessening unsuccessful fruit-setting by self-incompatibility and enhancing the fruit-setting rate.

TECHNICAL APPLICABILITY

Novel brassinosteroid analogous compounds possessing plant growth regulating activity expressed by compound (I) and compound (II) presented by the invention and the plant growth regulator containing them as active ingredients have an excellent durability on various plants in agricultural and horticultural fields, and present plant growth regulating actions, and are hence very useful industrially.

We claim:

1. A brassinosteroid derivative expressed in formula (II).

2. A plant growth regulator containing a brassinosteroid derivative expressed in formula (II)

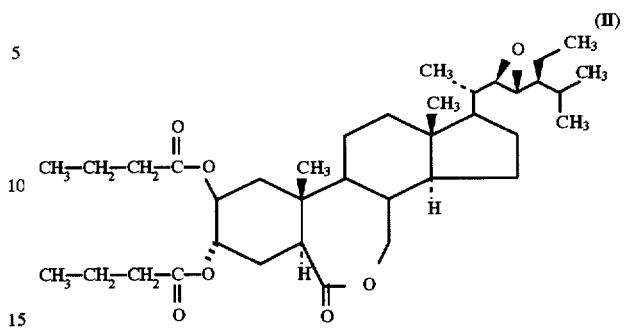

as active ingredient.

3. The plant growth regulator of claim 2 further comprising one or more additives selected from the group consisting of insecticides, fungicides, herbicides or fertilizers.

4. The plant growth regulator of claim 2 wherein the active ingredient is at a concentration of $1\times10^5$ ppm to 1 ppm.

5. The plant growth regulator of claim 4 wherein the active ingredient is at a concentration of $1\times10^3$ ppm to $1\times10^1$ ppm.

6. The plant growth regulator of claim 2 further comprising an agricultural chemical aid selected from the group consisting of spreading agents, emulsifiers, wetting agents, dispersants, binding agents and disintegrating agents.

7. The plant growth regulator of claim 6 wherein said plant growth regulator is in dosage form.

8. The plant growth regulator of claim 6 wherein the dosage form is selected from the group consisting of powder, granules, tablets, solids, wettable powder, emulsions and liquids.

9. The plant growth regulator of claim 2 further comprising one or more plant hormones.

* * * * *